(12) United States Patent
Al-Daous et al.

(10) Patent No.: US 11,292,755 B2
(45) Date of Patent: Apr. 5, 2022

(54) SYSTEMS AND PROCESSES FOR PRODUCING OLEFINS

(71) Applicant: Saudi Arabian Oil Company, Dhahran (SA)

(72) Inventors: Mohammed Abdulmajeed Al-Daous, Thuwal (SA); Hussam A. Bahlouli, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/901,344

(22) Filed: Jun. 15, 2020

(65) Prior Publication Data

US 2021/0387930 A1 Dec. 16, 2021

(51) Int. Cl.
| | |
|---|---|
| *C07C 5/333* | (2006.01) |
| *C07C 4/06* | (2006.01) |
| *C07C 5/05* | (2006.01) |
| *B01J 19/24* | (2006.01) |
| *B01J 23/75* | (2006.01) |

(Continued)

(52) U.S. Cl.
CPC ............ *C07C 5/3337* (2013.01); *B01J 19/245* (2013.01); *B01J 21/04* (2013.01); *B01J 23/75* (2013.01); *B01J 29/40* (2013.01); *B01J 29/605* (2013.01); *B01J 29/62* (2013.01); *C07C 4/06* (2013.01); *C07C 5/05* (2013.01); *B01J 2219/0004* (2013.01); *C07C 2521/04* (2013.01); *C07C 2523/75* (2013.01); *C07C 2529/40* (2013.01);

(Continued)

(58) Field of Classification Search
None
See application file for complete search history.

(56) References Cited

U.S. PATENT DOCUMENTS 4,523,045 A * 6/1985 Vora .......................... C07C 2/70
585/252
4,691,070 A * 9/1987 Nakamura ............... B01J 23/46
585/259

(Continued)

FOREIGN PATENT DOCUMENTS

| WO | 010111199 A2 | 9/2010 |
|---|---|---|
| WO | 2012016786 A1 | 2/2012 |

OTHER PUBLICATIONS

Wakui et al., "Dehydrogenative cracking of n-butane using double-stage reaction", Applied Catalysis A: General, vol. 230, pp. 195-202, 2002.

(Continued)

*Primary Examiner* — Philip Y Louie
(74) *Attorney, Agent, or Firm* — Dinsmore & Shohl LLP (57) ABSTRACT

Olefins may be produced from $C_4$-$C_6$ saturated hydrocarbons by systems and methods comprising passing a feed comprising $C_4$-$C_6$ saturated hydrocarbons and hydrogen into a dehydrogenation unit to produce a dehydrogenation effluent, passing at least a portion of the dehydrogenation effluent into a hydrogenation unit to produce a hydrogenation effluent, and passing at least a portion of the hydrogenation effluent into a cracking unit to produce a cracking effluent comprising olefins. The dehydrogenation unit includes a dehydrogenation catalyst, the hydrogenation unit includes a hydrogenation catalyst, and the cracking unit includes a cracking catalyst.

11 Claims, 2 Drawing Sheets

(51) Int. Cl.
  *B01J 29/62* (2006.01)
  *B01J 21/04* (2006.01)
  *B01J 29/40* (2006.01)
  *B01J 29/60* (2006.01)
(52) U.S. Cl.
  CPC ...... *C07C 2529/60* (2013.01); *C07C 2529/62* (2013.01)

(56) References Cited

U.S. PATENT DOCUMENTS

| | | | |
|---|---|---|---|
| 5,736,478 A * | 4/1998 | Cortright | B01J 29/61 502/74 |
| 6,159,272 A * | 12/2000 | Baker | B01D 53/002 95/39 |
| 7,087,155 B1 | 8/2006 | Dath et al. | |
| 7,692,057 B2 | 4/2010 | Xie et al. | |
| 8,258,357 B2 | 9/2012 | Dukandar et al. | |
| 9,024,100 B2 | 5/2015 | Wang et al. | |
| 2002/0002315 A1 | 1/2002 | Kelly et al. | |
| 2009/0112039 A1 | 4/2009 | Eng | |
| 2010/0240937 A1* | 9/2010 | Gartside | C07C 4/06 585/315 |
| 2010/0274063 A1* | 10/2010 | Wang | C10G 11/05 585/324 |

OTHER PUBLICATIONS

Wakui et al., "Dehydrogenative cracking of n-butane over modified HZSM-5 catalysts", Catalysis Letters, vol. 81, No. 1, Jul. 1-2, 2002.
International Search Report and Written Opinion dated Apr. 15, 2021 pertaining to International application No. PCT/US2020/066397 filed Dec. 21, 2020, 12 pgs.

* cited by examiner

SYSTEMS AND PROCESSES FOR PRODUCING OLEFINS

TECHNICAL FIELD

Embodiments of the present disclosure generally relate to systems and processes for producing olefinic petrochemicals and more specifically relate to systems and processes that utilize multiple reactor stages for producing olefinic petrochemicals.

BACKGROUND

Olefins (for example, ethylene, propylene, butenes, and butadiene) and BTX (benzene, toluene, and xylenes) are intermediates of the petrochemical industry, which annually supply hundreds of millions of metric tons of manufactured raw materials to many chemical industries including pharmaceuticals, plastics, optics, food, and dyes. Ethylene is used for plastic production with over 60 million tons of polyethylene made every year. Propylene is also a building block of many chemicals, with around 67% of all propylene currently produced each year being used to produce polypropylene.

SUMMARY

Commercially available processes for the production of propylene and other light olefins typically utilize thermal and catalytic cracking processes and "on-purpose" propylene production methods. Thermal and catalytic cracking processes namely fluid catalytic cracking (FCC) and steam cracking. On-purpose propylene production methods, which include propane dehydrogenation, methanol to olefins (MTO), methanol to olefins plus olefin cracking (MTO+OC) and methanol to propylene (MTP).

Conventional catalytic cracking processes of saturated hydrocarbons undergo a set of complicated reactions that may not be selective to the production of the desired product. Numerous side reactions can occur along with the main cracking reaction. Some of these side reactions are dehydrogenation, aromatization and hydrogen transfer. As such, there are needs for olefin production methods with increased selectivity while reducing undesired side products.

Embodiments of the present disclosure meet those needs by providing olefin production systems and methods that may increase selectivity while catalytically cracking saturated $C_4$-$C_6$ hydrocarbons to ethylene and propylene by reducing undesired side products. Against the above background, embodiments of the present disclosure are directed to systems and methods of producing olefins from $C_4$-$C_6$ saturated hydrocarbons by utilizing a three-stage process that includes a first dehydrogenation stage, a second selective hydrogenation stage, and a third olefin cracking stage. Together, the disclosed systems and methods may allow for increased selectivity when catalytically cracking saturated $C_4$-$C_6$ hydrocarbons to ethylene and propylene by reducing undesired side products.

According to one or more embodiments presently disclosed, olefins may be produced from $C_4$-$C_6$ saturated hydrocarbons by methods comprising passing a feed comprising $C_4$-$C_6$ saturated hydrocarbons and hydrogen into a dehydrogenation unit to produce a dehydrogenation effluent, passing at least a portion of the dehydrogenation effluent into a hydrogenation unit to produce a hydrogenation effluent, and passing at least a portion of the hydrogenation effluent into a cracking unit to produce a cracking effluent comprising olefins. The dehydrogenation unit includes a dehydrogenation catalyst, the hydrogenation unit includes a hydrogenation catalyst, and the cracking unit includes a cracking catalyst.

According to one or more embodiments presently disclosed, olefins may be produced from a system comprising a dehydrogenation unit comprising a dehydrogenation catalyst, the dehydrogenation catalyst comprising one or more of platinum and tin; a hydrogenation unit comprising a hydrogenation catalyst, the hydrogenation catalyst comprising from 0.25% to 7% by weight of a transition metal supported on a support comprising one or more of silica and alumina; and a cracking unit comprising a cracking catalyst, the cracking catalyst comprising a ZSM-5 catalyst.

These and other features, aspects, and advantages of the present disclosure will become better understood with reference to the following description and the appended claims.

Additional features and advantages of the embodiments presently described will be set forth in the detailed description which follows, and in part will be readily apparent to those skilled in the art from that description or recognized by practicing the embodiments presently described, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments presently described, and together with the description serve to explain the principles and operations of the claimed subject matter.

DETAILED DESCRIPTION

It should be understood that, as presently described, "catalyst systems" refer to materials which are catalytically active and may comprise a support material and one or more catalytically active materials, sometimes referred to as "the catalyst."

As used in this disclosure, a "reactor" refers to one or more vessels in which one or more chemical reactions may occur between one or more reactants optionally in the presence of one or more catalysts. For example, a reactor may include a tank or tubular reactor configured to operate as a batch reactor, a continuous stirred-tank reactor (CSTR), and a plug flow reactor, which will be subsequently described in more detail. Example reactors include packed bed reactors such as fixed bed reactors, and fluidized bed reactors. In embodiments presently described, a "unit" may include multiple reactors in series, such as where a plurality of vessels are connected which each contains the same or a different catalyst.

As used in this disclosure, a "separation unit" or separator refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and combinations of any of these devices. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation.

As used in this disclosure, "butanes" refers to all saturated $C_4$ chemical compounds, such as n-butane and isobutane.

As used in this disclosure, "butenes" refers to all singularly unsaturated $C_4$ chemical compounds, such as 1-butene, cis-2-butene, trans-2-butene, and isobutene.

Reference will now be made in detail to embodiments of systems and processes for producing olefins from $C_4$-$C_6$ saturated hydrocarbons. The systems and processes may include passing a feed comprising $C_4$-$C_6$ saturated hydrocarbons and hydrogen into a dehydrogenation unit to produce a dehydrogenation effluent, passing at least a portion of the dehydrogenation effluent into a hydrogenation unit to produce a hydrogenation effluent, and passing at least a portion of the hydrogenation effluent into a cracking unit to produce a cracking effluent comprising olefins. The dehydrogenation unit may include a dehydrogenation catalyst. The hydrogenation unit may include a hydrogenation catalyst, and the cracking unit may include a cracking catalyst.

Figure 1:
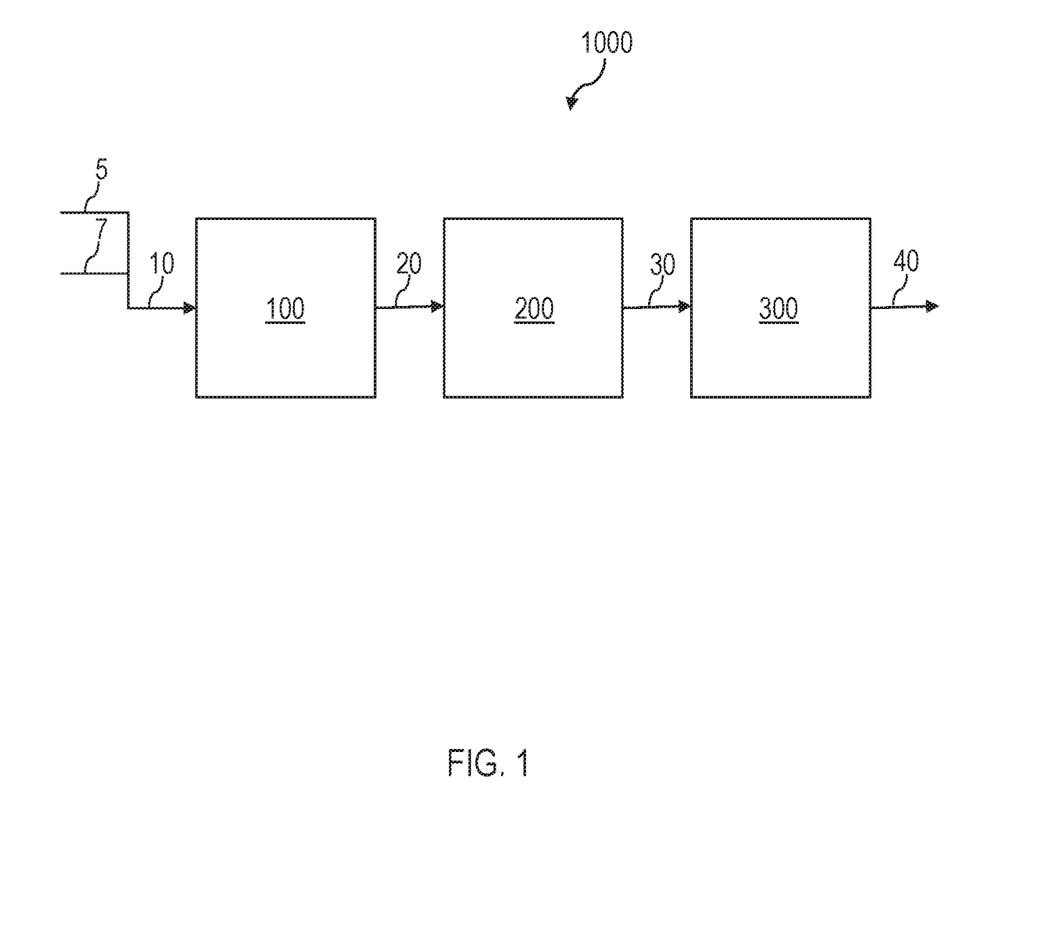
FIG. 1 is a schematic depiction of a system for producing olefins in accordance with one or more embodiments.

Referring to FIG. 1, an embodiment of a system configures to methods for producing olefins is depicted. As shown in FIG. 1, the system is configured for passing a feed 10 comprising $C_4$-$C_6$ saturated hydrocarbons and hydrogen into a dehydrogenation unit 100 to produce a dehydrogenation effluent 20, passing at least a portion of the dehydrogenation effluent 20 into a hydrogenation unit 200 to produce a hydrogenation effluent 30, and passing at least a portion of the hydrogenation effluent 30 into a cracking unit 300 to produce a cracking effluent 40 comprising olefins.

Embodiments of the present disclosure may specifically refer to a feed 10 comprising $C_4$-$C_6$ saturated hydrocarbons; however, suitable saturated hydrocarbon for the feed 10 may include one or more of alkanes (paraffins), alkylaromatics, and cycloalkanes (naphthenes), any of which may have from 2 to 30 or more carbon atoms. In embodiments, an initial feed 5 comprising $C_4$-$C_6$ saturated hydrocarbons can first be mixed with a hydrogen feed 7 to produce the feed 10 comprising $C_4$-$C_6$ saturated hydrocarbons and hydrogen. In embodiments, the feed 10 may further include a carrier gas. The carrier gas may be nitrogen, argon, helium, or combinations of these gases. In an exemplary embodiments, the carrier gas may be a mixture containing 5% to 100% by volume hydrogen, with the balance nitrogen.

Optional pretreatment steps are contemplated for the feed 10. For example, the initial feed 5 containing $C_4$-$C_6$ saturated hydrocarbons may first be optionally passed through a pump (not shown) to create a pressurized initial feed 5 before being mixed with the hydrogen feed 7 to produce the feed 10 comprising $C_4$-$C_6$ saturated hydrocarbons and hydrogen. In other embodiments, the initial feed 5 or pressurized initial feed 5 may be passed through a heater (not shown) to create a preheated initial feed 5 or preheated or a preheated, pressurized initial feed 5 before being mixed with the hydrogen feed 7. In embodiments, the feed 10 comprising $C_4$-$C_6$ saturated hydrocarbons and hydrogen may be optionally passed through a pump (not shown) to create a pressurized feed 10. In embodiments, the feed 10 comprising $C_4$-$C_6$ saturated hydrocarbons and hydrogen may be passed through a heater (not shown) to create a preheated feed 10.

In certain embodiments, the process may include preheating the feed 10 to a preheat temperature of at least 100° C., such as from 100° C. to 300° C., or from 100° C. to 250° C., or from 100° C. to 200° C., either before or after mixing the initial feed 5 with the hydrogen feed 7. In particular, the preheat temperature may be chosen to be sufficiently high to attain a feed temperature that is within 100° C., or within 50° C., or within 20° C. of the reaction temperature in the dehydrogenation unit 100 while being sufficiently low to avoid reactions within the feed 10 outside the catalyst zone in the dehydrogenation unit 100.

In embodiments, the hydrogen may be imported hydrogen, recycled hydrogen from one or more downstream units, or combinations. Like the initial feed, the hydrogen feed 7 to be mixed with the initial feed 5 optionally may be passed through a heater (not shown) to create a preheated hydrogen stream or may also be pressurized, for example, by a pump (not shown), to produce a preheated and pressurized hydrogen feed 7, before being mixed with the initial feed 5, the pressurized initial feed 5, or the preheated and pressurized initial feed 5. In some embodiments, the heater may serve to heat the hydrogen feed 7 (or pressurized hydrogen feed 7) to a temperature of at least 100° C., such as from 100° C. to 300° C., or from 100° C. to 250° C., or from 100° C. to 200° C.

As shown in FIG. 1, the system is configured for passing the feed 10 comprising $C_4$-$C_6$ saturated hydrocarbons and hydrogen to a dehydrogenation unit 100. Dehydrogenation is a chemical reaction that involves the removing a hydrogen atom from an organic hydrocarbon molecule to produce a double bond in the organic hydrocarbon. Dehydrogenation converts species such as alkanes, which are relatively inert and thus low-valued, to olefins, which are more reactive and generally more valuable. For example, the dehydrogenation of paraffins and iso-paraffins may result in valuable products, such as when n-pentane or isopentane are converted to pentene and isoprene, respectively. Additionally, alkenes and alkadienes are valuable precursors for the production of aldehydes, alcohols, polymers, and aromatics. The dehydrogenation unit 100 presently described dehydrogenates saturated hydrocarbon feedstock to produce linear alkenes with little or no simultaneous cracking or isomerization reactions that could tend to produce smaller or branched hydrocarbon chains, respectively. In embodiments, the dehydrogenation reactor 100 is able to produce linear butenes such as 1-butene, trans-2-butene, and cis-2-butene. The dehydrogenation process generally produces the diolefin 1,3-butadiene as a side product.

The feed 10 containing the $C_4$-$C_6$ saturated hydrocarbons and hydrogen may be passed to a dehydrogenation unit 100 at a temperature from 500° C. to 575° C., from 500° C. to 550° C., from 500° C. to 525° C., from 525° C. to 575° C., from 525° C. to 550° C., or from 550° C. to 575° C., at a hydrogen partial pressure from 0.01 barg (1 kPa) to 2 barg (200 kPa). The dehydrogenation unit 100, which includes a dehydrogenation reactor described subsequently in more detail, comprises a dehydrogenation catalyst that, when contacted with the feed 10, produces a dehydrogenation effluent 20 resulting from the dehydrogenation of the feed 10.

The dehydrogenation unit 100 may include one reactor or multiple reaction vessels in parallel or series, which are collectively referred to as the dehydrogenation unit 100. For example, a reactor of the dehydrogenation unit 100 can include a plurality of reaction vessels, each containing an effective amount of one or more dehydrogenation catalysts.

Each of the one or more reactions of the dehydrogenation unit 100 may operate under parameters effective for dehydrogenation of the feed 10. For example, in some embodiments, the dehydrogenation unit 100 may operate at a temperature from 500° C. to 575° C., from 500° C. to 550° C., from 500° C. to 525° C., from 525° C. to 575° C., from 525° C. to 550° C., or from 550° C. to 575° C. In some embodiments, the dehydrogenation unit 100 can operate at a hydrogen partial pressure from 0.01 barg (1 kPa) to 2 barg (200 kPa). Further hydrogen partial pressure ranges include from 0.01 barg (1 kPa) to 1 barg (100 kPa), from 0.01 barg (1 kPa) to 2 barg (200 kPa), from 0.05 barg (5 kPa) to 1 barg (100 kPa), from 0.05 barg (5 kPa) to 2 barg (200 kPa), from 0.1 barg (10 kPa) to 1 barg (100 kPa), from 0.1 barg (10 kPa) to 2 barg (200 kPa), and from 0.5 barg (50 kPa) to 2 barg (200 kPa).

As stated previously, the dehydrogenation unit 100 may include a dehydrogenation catalyst that, when contacted with the feed 10, produces a dehydrogenation effluent 20 resulting from the dehydrogenation of the feed 10. The dehydrogenation catalyst may include catalysts that are active and selective for alkane dehydrogenation. In embodiments, the dehydrogenation catalyst may include a L-zeolite optionally treated with an active metal such as platinum, tin, or both. In embodiments, the dehydrogenation catalysts utilized may include heterogeneous catalysts comprising platinum group metals for the dehydrogenation of liquid or gaseous hydrocarbons. In embodiments, the catalyst may include tin, which may inhibit isomerization and cracking activities normally concurrently experienced in the use of unmodified noble metal composites in the processing of hydrocarbon feeds in the vapor or liquid phase at elevated temperatures. The dehydrogenation catalyst may further include an alkali metal or an alkaline earth metal component, which may improve one or more of the activity, selectivity, and stability of the catalyst.

The dehydrogenation catalyst may further include a porous support. The porous support may include activated carbon, coke, or charcoal; silica or silica gel, silicon carbide, clays and silicates; ceramics, porcelain, crushed firebrick, bauxite; refractory inorganic oxides such as alumina, titania, zirconia and the like; crystalline zeolite silicates; spinels; and combinations.

In embodiments, the isomerization or cracking activity of the selective dehydrogenation catalysts is maintained at less than 5 mole %, or less than 4 mole %, or less than 3 mole % of the feedstock, measured as the number of moles of isomerized or cracked hydrocarbons in the product relative to the feedstock.

Referring still to FIG. 1, the system is configured for passing at least a portion of the dehydrogenation effluent 20 into a hydrogenation unit 200 to produce a hydrogenation effluent 30. The dehydrogenation effluent 20 may comprise hydrogen, $C_4$-$C_6$ saturated hydrocarbons that did not react in the dehydrogenation unit 100, and corresponding olefins and dienes of the $C_4$-$C_6$ saturated hydrocarbons that were dehydrogenated in the dehydrogenation unit 100. In embodiments, the dehydrogenation effluent 20 may include one or more of butenes, 1,3-butadiene, hydrogen, unreacted n-butane, and nitrogen.

Within dehydrogenation reactions of hydrocarbon mixtures, dienes are present in equilibrium amounts as a significant byproduct. The presence of dienes in a hydrocarbon mixture intended for further cracking may reduce the quantity of olefins produced upon cracking. Moreover, dienes are more reactive than olefins making them more susceptible to aromatization and oligomerization over solid acid catalysts, which in turn may lead to faster catalyst deactivation. Accordingly, embodiments of the disclosed processes incorporate a selective hydrogenation stage before the olefin cracking reaction stage. The inclusion of the selective hydrogenation stage as an intermediate stage of a three-stage process is believed to increase the olefins yield upon cracking and to provide longer stability to the cracking catalyst. The selective hydrogenation stage may hydrogenate back to linear mono-olefins a portion or all of the dienes produced by the dehydrogenation reaction in the dehydrogenation unit 100.

The hydrogenation unit 200 may include one reactor or multiple reaction vessels in parallel or series, which are collectively referred to as the hydrogenation unit 200. For example, a reactor of the hydrogenation unit 200 can include a plurality of reaction vessels, each containing an effective amount of one or more hydrogenation catalysts. In an alternative embodiment, the hydrogenation unit 200 may include one or more separation zones, each containing an effective amount of hydrogenation catalyst.

The hydrogenation reactor 200 may operate under parameters effective for hydrogenation of the dehydrogenation effluent 20. For example, in some embodiments, the hydrogenation reactor 200 may operate at a temperature from 100° C. to 180° C., from 100° C. to 140° C., from 100° C. to 120° C., from 120° C. to 180° C., from 120° C. to 140° C., or from 140° C. to 180° C. In some embodiments, the hydrogenation reactor 200 can operate at atmospheric pressure.

As stated previously, the hydrogenation unit 200 may include a hydrogenation catalyst that, when contacted with the dehydrogenation effluent 20, produces a hydrogenation effluent 30 resulting from the hydrogenation of the dehydrogenation effluent 20. The hydrogenation catalysts may include catalysts that are active and selective for converting dienes into olefins. In embodiments, the hydrogenation catalysts may be transition metal catalysts supported on silica or alumina supports known in the art. In embodiments, the transitional metal of the hydrogenation catalyst may include cobalt (Co), nickel (Ni), or iron (Fe). The hydrogenation catalyst may include from 0.25% to 7% by weight of the transition metal, based on the total weight of the hydrogenation catalyst. In further embodiments, hydrogenation catalyst may include from 0.25% to 7%, from 0.25% to 5%, from 0.25% to 3%, from 0.25% to 1%, from 1% to 7%, from 1% to 5%, from 1% to 3%, from 3% to 7%, from 3% to 5%, or from 5% to 7%, by weight of the transition metal, based on the total weight of the hydrogenation catalyst. In one embodiment, the hydrogenation catalyst may include 0.5% by weight cobalt supported on an alpha-alumina support.

Referring still to FIG. 1, the system is configured for passing at least a portion of the hydrogenation effluent 30 into a cracking unit 300 to produce a cracking effluent 40 containing olefins. In embodiments, the cracking catalyst may promote the cracking reactions of the butenes to produce shorter hydrocarbons such as methane, ethane, ethylene, propane, and propylene. The hydrogenation effluent 30 may include one or more of n-butane; linear butenes; hydrogen and nitrogen carrier gas. In embodiments, the cracking stage of the presently-disclosed systems may allow for the olefins (butenes) to be cracked and converted to ethylene and propylene with more than 45% combined yield with the formation of small amounts of BTX aromatics and isobutene over the cracking catalyst.

The cracking stage of the presently disclosed methods includes the cracking of olefins contained in a stream with a decreased amount of dienes such as 1,3-butadiene, or even substantially no dienes than would be present if the intermediate hydrogenation stage were omitted. The cracking stream in embodiments may contain olefins, nitrogen, hydrogen and saturated hydrocarbons. In embodiments, the catalytic cracking rate of olefins may therefore be relatively higher than that of saturated hydrocarbons (alkanes) with the same number of carbon atoms over acidic catalysts and under the same conditions.

The cracking unit 300 may include one reactor or multiple reaction vessels in parallel or series, which are collectively referred to as the cracking unit 300. For example, a reactor of the cracking unit 300 can include a plurality of reaction vessels, each containing an effective amount of one or more cracking catalysts. The cracking unit 300 may include in different type of reactors, including fixed bed or fluidized bed reactor. In some embodiments, utilizing a fixed bed reactor may produce a relatively higher yield of desired products and require relatively lower cracking reaction temperature.

A reactor of the cracking unit 300 may operate under parameters effective for cracking of the hydrogenation effluent 30. For example, in some embodiments, the cracking unit 300 may operate at a temperature from 400° C. to 600° C., from 400° C. to 550° C., from 400° C. to 500° C., from 400° C. to 450° C., from 450° C. to 600° C., from 450° C. to 550° C., from 450° C. to 500° C., from 500° C. to 600° C., from 500° C. to 550° C., or from 550° C. to 600° C. In some embodiments, the reactor of the cracking unit 300 may operate at atmospheric pressure.

Depending on the operating conditions (temperature, partial pressure, etc.), olefin chain length, reaction space velocity, acid strength and silica ($SiO_2$) to alumina ($Al_2O_3$) ratio of the zeolite catalyst, either monomolecular (protolytic) or the desired bimolecular (oligomerization cracking) olefin cracking mechanisms may be favored. In embodiments, the silica ($SiO_2$) to alumina ($Al_2O_3$) ratio of the zeolite may be from 20 to 300, from 20 to 100, from 20 to 50, from 50 to 300, or from 50 to 100. In embodiments, the silica ($SiO_2$) to alumina ($Al_2O_3$) ratio of the zeolite may allow for a preference for oligomerization-cracking reaction path of the butenes, which may in turn increase the yield of ethylene and propylene in the product stream.

In embodiments, the cracking catalyst may be a ZSM-5 catalyst. ZSM-5 zeolite is an aluminosilicate zeolite of an mordenite framework inverted (MFI) developed by Mobil and belonging to the pentasil family of zeolites, so called owing to rings of five silicon atoms prevalent in the zeolite framework. ZSM-5 and has a nominal chemical formula of $Na_nAl_nSi_{96-n}O_{192}.16H_2O$, where subscript n is from 0 to 27. The subscript n in the ZSM-5 thus indicates a silica-to-alumina ratio (SAR) of the zeolite. ZSM-5 zeolites may be produced having silica-to-alumina ratios as small as 12 and as large as approaching infinity if nearly all of the aluminum atoms are replaced by silicon. The sodium ions in ZSM-5, of equal number to the number of aluminum atoms, maintain neutral charge in the zeolite.

The ZSM-5 may comprise porosity. A micropore volume represents the specific volume corresponding to the microporous structure of ZSM-5. The pore size ranges for micropores are in conformity with conventionally understood size ranges for such pore classifications with micropores representing pores under 2 nanometers (nm) in diameter. A total pore volume would additionally include any mesopores and macropores if present.

The surface area of the pores of the ZSM-5 individually affect the butenes cracking reaction in the cracking unit 300. An increased surface area provides increased interaction between the individual catalyst components and the constituents of the hydrogenation effluent passed into the cracking unit thereby allowing for increased conversion activity.

In one or more embodiments, the ZSM-5 may have a surface area defined by a Brunauer-Emmett-Teller (BET) analysis ($S_{BET}$) of at least 300 square meters per gram ($m^2/g$), a $S_{BET}$ surface area of at least 325 $m^2/g$, or a $S_{BET}$ surface area of at least 350 $m^2/g$. In one or more embodiments, the ZSM-5 zeolite catalyst is a commercially available ZSM-5. For example, the ZSM-5 may be CBV3024E from Zeolyst International (Conshohocken, Pa., USA).

Figure 2:
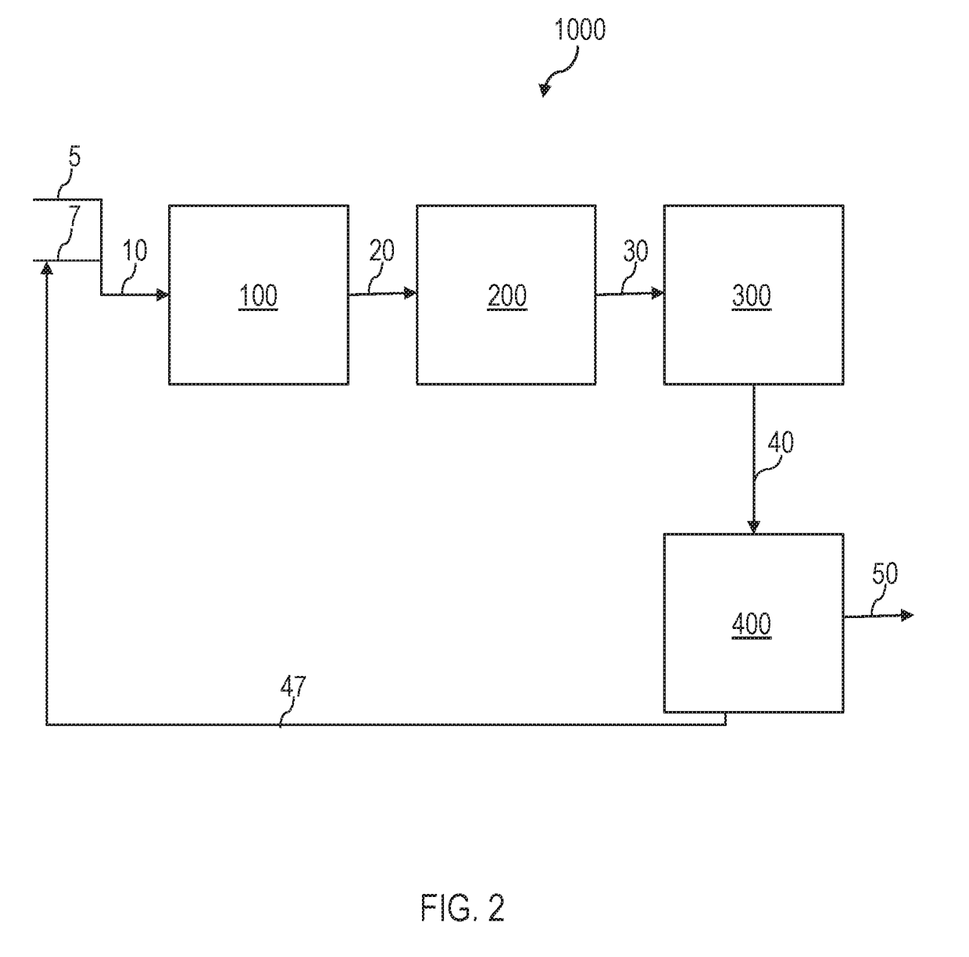
FIG. 2 is a schematic depiction of a system for producing olefins in accordance with one or more embodiments.

Referring now to FIG. 2, the cracking effluent 40 may be fed to at least one downstream unit for further processing. In some embodiments, the cracking effluent 40 may be recycled back into the cracking unit 300 and further converted to ethylene and propylene. In embodiments, the cracking effluent 40 may be fed to a separation unit 400. The separation unit 400 may convert the cracking effluent 40 into one or more product streams comprising olefins, aromatics, or combinations thereof. In some embodiments, the one or more product streams may include BTX (benzene, toluene and xylene). In the embodiments of FIG. 1, the separator 400 may yield methane 21, ethylene and ethane 22, propene and propane 23, butadiene 24, mixed butenes 25, pyrolysis gasoline 26 and pyrolysis fuel oil 27. Any suitable separation vessel is contemplated that can split the products of the cracking effluent 40 into the desired products. Various vessels are contemplated for the separation unit 400. In certain embodiments, the separation unit 400 may include a flash vessel, a fractionator, a distillation vessel or combinations thereof. In some embodiments, the separation unit 400 may include one or more flash vessels. In certain embodiments, the flash vessel is a flash drum. In some embodiments, the separation unit 400 may include one or more distillation vessels. The distillation vessel can be a distillation tower, such as a vacuum distillation tower. Moreover, further embodiments of the separation unit 400 may include gas-liquid separators, oil-liquid separators, or combinations.

Additionally, the separation unit 400 may further produce another hydrogen stream 47 that can be recycled back for mixing with the feed 10. In specific embodiments, the hydrogen stream 47 is passed to a hydrogen purification unit (not shown) to produce a treated hydrogen stream. The treated hydrogen stream may then be transferred for mixing with the hydrogen feed 7. In the embodiments of FIG. 2, product streams 50 and 47 are shown for illustration and should not be construed as the only product streams produced in the separation unit 400.

The features of the present embodiments will be further illustrated in the Examples that follow.

EXAMPLES

The following Examples illustrate one or more embodiments of the present disclosure. It should be understood that the Examples are not intended to limit the scope of the disclosure or the appended claims to the Examples themselves.

Example 1

Preparation of L-Zeolite

In Example 1, a commercially-available L-Zeolite (grade HSZ-500, supplied by Tosoh Corporation) was thermally treated as follows under static air. First, the commercial L-Zeolite, starting at room temperature, was heated to a temperature of 120° C. at a ramping rate of 5° C. per minute. Once the temperature of 120° C. was reached, the commercial L-Zeolite was calcined at this temperature for 3 hours. Then, the commercial L-Zeolite was heated to a temperature of 600° C. at a ramping rate of 2° C. per minute. Once the temperature of 600° C. was reached, the commercial L-Zeolite was calcined at this temperature for 20 hours. The obtained product was a calcined L-Zeolite with BET-surface area of 290 $m^2/g$.

Example 2

Preparation of α-Alumina

Example 2 was a commercially-available α-Alumina supplied by Alfa Aesar, which was α-phase with BET-surface area of 3 $m^2/g$ to 4 $m^2/g$.

Example 3

Preparation of ZSM-5 Zeolite

In Example 3, a commercially-available ZSM-5-Zeolite (supplied by Zeolyst International) was thermally treated as follows under static air. First, the commercial L-Zeolite, starting at room temperature, was heated to a temperature of 120° C. at a ramping rate of 5° C. per minute. Once the temperature of 120° C. was reached, the commercially-available ZSM-5-Zeolite was calcined at this temperature for 3 hours. Then, the commercially-available ZSM-5-Zeolite was heated to a temperature of 600° C. at a ramping rate of 2° C. per minute. Once the temperature of 600° C. was reached, the commercially-available ZSM-5-Zeolite was calcined at this temperature for 24 hours. The obtained product was a calcined commercially-available ZSM-5-Zeolite with BET-surface area of 280 $m^2/g$.

Example 4

Preparation of PtSn/K-L Zeolite, Catalyst A

In Example 4, 10.21 grams of potassium nitrate ($KNO_3$) were dissolved in 250 milliliters deionized water to produce a solution, and 20 grams of the calcined L-Zeolite of Example 1 were dispersed in the solution. The solution was added to the calcined L-Zeolite of Example 1 at once to produce a dispersion, the dispersion was mixed at room temperature for 3 hours, and the solids were then filtered from the solution and washed with 250 milliliters of deionized water. The solids were dried further at 120° C. for 24 hours. 20 grams of the calcined treated K-L Zeolite were loaded with 0.5% by weight tin (Sn) by wetness impregnation by dissolving 0.24 grams of tin chloride ($SnCl_2 \cdot 2H_2O$) in 50 milliliters ethanol, adding this solution to the K-L Zeolite at once, and stirring at room temperature for 3 hours until a homogenous dispersion was obtained. The solids were then recovered and dried by roto-evaporation and dried at 120° C. for 24 hours. 20 grams of the dried solid were then loaded with 1.0% by weight platinum (Pt) by dissolving 0.39 grams of tetraammineplatinum(II) nitrate ($Pt(NH_3)_4(NO_3)_2$) in 20 milliliters of de-ionized water, adding the platinum solution to the solid powder, and mixing at 85° C. for 3 hours until a homogenous dispersion was obtained. These solids were then recovered by roto-evaporation. The solids were dried further at 120° C. for 24 hours. The dried sample was calcined at 425° C. for 16 hours in air.

Example 5

Preparation of 0.01% Co/α-Alumina, Catalyst B

In Example 5, 5.0 grams of the α-alumina of Example 2 were loaded with 0.01% by weight cobalt (Co) via wetness impregnation whereby 0.0021 grams of cobalt acetate ($Co(CH_3COO)_2$) was dissolved in 5 milliliters deionized water. The cobalt solution was added to the solid α-alumina at once, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 6

Preparation of 0.1% Co/α-Alumina, Catalyst C

In Example 6, 5.0 grams of α-alumina of Example 2 were loaded with 0.1% by weight cobalt (Co) via wetness impregnation whereby 0.021 grams of cobalt acetate ($Co(CH_3COO)_2$) were dissolved in 5 milliliters deionized water. The cobalt solution was added to the solid α-alumina, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 7

Preparation of 0.25% Co/α-Alumina, Catalyst D

In Example 7, 5.0 grams of α-Alumina of Example 2 were loaded with 0.25% by weight cobalt (Co) via wetness impregnation whereby 0.053 grams of cobalt acetate ($Co(CH_3COO)_2$) were dissolved in 5 milliliters deionized water. The cobalt solution was added to the solid α-alumina, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 8

Preparation of 0.5% Co/α-Alumina, Catalyst E

In Example 8, 5.0 grams of α-Alumina of Example 2 were loaded with 0.5% by weight cobalt (Co) via wetness impregnation whereby 0.106 grams of cobalt acetate ($Co(CH_3COO)_2$) were dissolved in 5 milliliters deionized water. The cobalt solution was added to the solid α-Alumina, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 9

Preparation of 1.0% Co/α-Alumina, Catalyst F

In Example 9, 5.0 grams of α-Alumina of Example 2 were loaded with 1.0% by weight cobalt (Co) via wetness impregnation whereby 0.211 grams of cobalt acetate (Co(CH$_3$COO)$_2$) were dissolved in 5 milliliters deionized water. The cobalt solution was added to the solid α-alumina, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 10

Preparation of 3.0% Co/α-Alumina, Catalyst G

In Example 10, 5.0 grams of α-Alumina of Example 2 were loaded with 3.0% by weight cobalt (Co) via wetness impregnation whereby 0.620 grams of cobalt acetate (Co(CH$_3$COO)$_2$) were dissolved in 5 milliliters deionized water. The cobalt solution was added to the solid α-alumina, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 11

Preparation of 7.0% Co/α-Alumina, Catalyst H

In Example 11, 5.0 grams of α-Alumina of Example 2 were loaded with 7.0% by weight cobalt (Co). The method used was wetness impregnation whereby 1.6 grams of cobalt acetate (Co(CH$_3$COO)$_2$) were dissolved in 5 milliliters deionized water. The cobalt solution was added to the solid α-alumina, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 12

Preparation of 15% Co/α-Alumina, Catalyst I

In Example 12, 5.0 grams of α-Alumina of Example 2 were loaded with 15% by weight cobalt (Co) via wetness impregnation whereby 3.1 grams of cobalt acetate (Co(CH$_3$COO)$_2$) were dissolved in 5 milliliters deionized water. The cobalt solution was added to the solid α-alumina at once, mixed at room temperature for 3 hours until a homogenous dispersion was obtained, and the solid product was then recovered by roto-evaporation. The solid was dried further at 120° C. for 24 hours. The dried sample was calcined at 450° C. for 5 hours in air.

Example 13

Catalyst A Treatment and Activation

In Example 13, Catalyst A (of Example 4) was activated before testing in stage-one reactor of a three-stage reactor system. Catalyst A was pressed at 7 metric tons (7000 kilograms) pressure to form tablets and crushed and sieved to form 200 to 500 micrometer granules. The granules (approximately 1.0 cm$^3$, 0.5 grams) were packed into a tubular Hastelloy-X reactor, which was 510 mm in length and with 5 mm internal diameter, and a thermocouple was immersed into the catalyst bed. Air (approx. 100 cm$^3$/min) was passed over the catalyst and the temperature was raised to 425° C. at the rate of 2.5° C./min and kept at 425° C. for at least 4 hours. The catalyst was then purged with nitrogen (approx. 100 cm$^3$/min) for 60 minutes while lowering the temperature to 400° C. before flowing hydrogen at 50 cm$^3$/min for 4 hours. The temperature was then raised to the reaction temperature at a rate of 5° C./min.

Example 14

Catalyst B-I Treatment and Activation

In Example 14, Catalysts B-I were activated before testing in a stage-two reactor of a three-stage reactor system. The catalysts as prepared in the examples were pressed at 7 metric tons (7000 kilograms) pressure to form tablets and crushed and sieved to form 200 micrometer to 500 micrometer granules. The granules (approx. 0.13 cm$^3$, 0.5 grams) were packed into a tubular steel reactor which was 110 mm in length and with 9 mm internal diameter. Air (approx. 100 cm$^3$/min) was passed over the catalyst and the temperature was raised to 180° C. and kept at 180° C. for at least 4 hours. The catalyst was then purged with nitrogen (approx. 100 cm$^3$/min) for 60 minutes before flowing hydrogen at 50 cm$^3$/min for 4 hours. Then, temperature was adjusted to the reaction temperature.

Example 15

ZSM-5 Catalyst Treatment and Activation

In Example 15, an olefin cracking catalyst was activated before testing in stage-three reactor of a three-stage reactor system. The olefin cracking catalyst was pressed at 7 metric tons (7000 kilograms) pressure to form tablets and crushed and sieved to form 200 to 500 micrometer granules. The granules (approx. 0.7 cm$^3$, 0.5 grams) were packed into a tubular Hastelloy-X reactor, which was 510 mm in length and with 5 mm internal diameter, and a thermocouple was immersed into the catalyst bed. Air (approx. 100 cm$^3$/min) was passed over the catalyst and the temperature was raised to 500° C. at the rate of 2.5° C./min and kept at 500° C. for at least 4 hours. The catalyst was then purged with nitrogen (approx. 100 cm$^3$/min) for 60 minutes while lowering the temperature to 400° C. before flowing hydrogen at 50 cm$^3$/min for 4 hours. The temperature was then raised to the reaction temperature at a rate of 5° C./min.

Example 16 n-Butane Dehydrogenation

Catalyst A was used for n-butane dehydrogenation in stage-one reactor to produce linear butenes (1-butane, trans 2-butene, and cis 2-butene) with butadiene as the main side product. The activity values listed were measured after 10 hours on stream. A total of 122.5 mL/min diluting carrier gas mixture of hydrogen and nitrogen were used for the entire reaction time. Table 1 lists the activity values obtained using the mentioned carrier gas compositions, which gave maximum yields. The conversion of n-butane and the selectivity for linear butenes (1-butene+cis-2-butene+trans-2-butene) were found to have an optimum value when the WHSV=1 $h^{-1}$ was used for the n-butane dehydrogenation reaction.

TABLE 1

Effluent of stage-1 n-Butane dehydrogenation reaction over catalyst A at 550° C., after 10 hours on stream, under atmospheric pressure, liquid n-butane flow 0.5 g/h, $H_2$:$N_2$ composition 7.5:115 mL/min, 0.5 g catalyst and WHSV = 1$h^{-1}$.

| Dehydrogenation of n-butane over Catalyst A | |
|---|---|
| n-Butane conversion, % | 75.2 |
| Product Distribution, mol/100 mol converted | |
| Methane | 0.26 |
| Ethane | 0.16 |
| Ethylene | 0.00 |
| Propane | 0.13 |
| Propylene | 0.19 |
| Iso-Butane | 0.04 |
| n-Butane | 24.83 |
| Butenes[a] | 64.69 |
| Iso-Butylene | 0.27 |
| 1,3-Butadiene | 9.44 |
| C5+[b] | 0.00 |
| BTX[c] | 0.00 |

[a]Butenes: 1-Butene + cis-2-Butene + trans-2-Butene
[b]C5: n-Pentane + iso-Pentane + 1-Pentene + cis-2-Pentene + trans-2-Pentene + 3-Methyl-1-butene + 2-Methyl-1-butene + 2-Methyl-2-butene
[c]BTX: Benzene, Toluene, and Xylene Example 17

Selective Diene Hydrogenation

The activated catalysts D-H of Examples 7-11, respectively, were tested in the hydrogenation reactor for the selective hydrogenation of butadiene to linear butenes (1-butene and trans & cis 2-butenes). The feed for this second-stage reactor was the effluent of the first-stage reactor (of Example 16), which primarily contained butenes, butadiene, hydrogen, unreacted n-butane and nitrogen. The results obtained and conditions used are listed in Table 2. The activity values listed were measured after 10 hours on stream which reflects the relatively high stability of the catalysts with time on stream. Table 2 lists the activity values where the amounts of n-butane in the reaction stream were found to increase slightly with increasing amounts of cobalt metal on the catalyst and over catalyst with low cobalt metal content, the amount of n-butane remained the same as was originally in the feed stream. Selectivity and yield for linear butenes (1-Butene+cis-2-Butene+trans-2 Butene) increased by more than 10 percent over the hydrogenation catalysts with 0.25% by weight Co with no detectable amounts of butadiene and the optimum overall hydrogenation reaction performance was obtained when using WHSV=1 $h^{-1}$.

TABLE 2

Effluent of stage-2 butadiene selective hydrogenation reaction over catalysts D-H at 180° C., after 10 hours on stream, under atmospheric pressure, 0.5 g catalyst.

| Catalyst | A | D | E | F | G | H |
|---|---|---|---|---|---|---|
| Cobalt wt. % | 0.0 | 0.25 | 0.5 | 1.0 | 3.0 | 7.0 |
| Product Distribution, mol/100 mol converted | | | | | | |
| Methane | 0.26 | 0.23 | 0.32 | 0.32 | 0.39 | 0.43 |
| Ethane | 0.16 | 0.14 | 0.14 | 0.15 | 0.24 | 0.26 |
| Ethylene | 0.00 | 0.00 | 0.04 | 0.07 | 0.01 | 0.00 |
| Propane | 0.13 | 0.12 | 0.11 | 0.12 | 0.19 | 0.21 |
| Propylene | 0.19 | 0.24 | 0.30 | 0.49 | 0.40 | 0.44 |
| Iso-Butane | 0.04 | 0.03 | 0.05 | 0.07 | 0.12 | 0.10 |
| n-Butane | 24.83 | 24.97 | 27.67 | 29.35 | 30.19 | 33.14 |
| Butenes[a] | 64.69 | 73.97 | 70.86 | 68.92 | 68.00 | 65.00 |
| Iso-Butylene | 0.27 | 0.32 | 0.50 | 0.49 | 0.42 | 0.38 |
| 1,3-Butadiene | 9.44 | 0.00 | 0.00 | 0.02 | 0.05 | 0.05 |
| C5+[b] | 0.00 | 0.00 | 0.00 | 0.00 | 0.00 | 0.00 |
| BTX[c] | 0.00 | 0.00 | 0.00 | 0.00 | 0.00 | 0.00 |
| Total | 100.0 | 100.0 | 100.0 | 100.0 | 100.0 | 100.0 |

[a]Butenes: 1-butene + cis-2-butene + trans-2-butene
[b]C5+: n-pentane + iso-pentane + 1-pentene + cis-2-pentene + trans-2-pentene + 3-methyl-1-butene + 2-methyl-1-butene + 2-methyl-2-butene
[c]BTX: Benzene, Toluene, and Xylene

Example 18

Butenes Cracking

ZSM-5 zeolite (with silica/alumina ratio of 280 m²/g) catalyst was activated as described in Example 15 above and used for butenes cracking reaction in the third-stage reactor. The feed stream used for the third-stage reactor was the effluent of the second-stage reactor (of Example 17), containing mainly n-butane; linear butenes; hydrogen and nitrogen carrier gas. The reaction results obtained and conditions used are given in Table 3. The values listed in Table 3 are those obtained from a reaction complete process where dehydrogenation of n-butane was carried out in the stage-1 reactor over Catalyst A, the effluent of stage-1 was the directly fed to the stage-2 reactor to selectively hydrogenate butadiene over a 0.5% Co/α-alumina catalyst (Catalyst D), and the effluent of stage-2 was directly fed to the stage-3 reactor to crack the butenes over a ZSM-5 catalyst. The activity values listed were measured after 10 hours on stream which reflects the relatively high stability of the catalysts with time on stream. The conversion of butenes and the selectivity for cracked product (ethylene, propylene) were found to have an optimum point when the WHSV=1 $h^{-1}$ is used for the third reactor.

TABLE 3

Process effluent with stage-3 butenes cracking reaction at 500° C., after 10 hours on stream, atmospheric pressure, 0.5 g catalyst and WHSV =1 $h^{-1}$.

| Stage | 1 | 2 | 3 |
|---|---|---|---|
| Reaction | Dehydrogenation | Hydrogenation | Cracking |
| Catalyst | A | D | ZSM-5 |
| Product Distribution, mol/100 mol converted | | | |
| Methane | 0.26 | 0.32 | 1.00 |
| Ethane | 0.16 | 0.14 | 0.41 |
| Ethylene | 0.00 | 0.04 | 11.25 |
| Propane | 0.13 | 0.11 | 0.94 |
| Propylene | 0.19 | 0.30 | 34.42 |
| Iso-Butane | 0.04 | 0.05 | 1.50 |
| n-Butane | 25.10 | 28.17 | 23.74 |
| Butenes[a] | 64.69 | 70.86 | 12.37 |
| Iso-Butylene | 0.27 | 0.50 | 8.80 |
| 1,3-Butadiene | 9.44 | 0.00 | 0.00 |
| C5+[b] | 0.00 | 0.00 | 2.65 |
| BTX[c] | 0.00 | 0.00 | 2.94 |
| Total | 100.0 | 100.0 | 100.0 |

[a]Butenes: 1-butene + cis-2-butene + trans-2-butene
[b]C5+: n-pentane + iso-pentane + 1-pentene + cis-2-pentene + trans-2-pentene + 3-methyl-1-butene + 2-methyl-1-butene + 2-methyl-2-butene
[c]BTX: Benzene, Toluene, and Xylene The results of Table 3 show that the olefins (butenes) were cracked and converted successively to ethylene and propylene with more than 45% combined yield (11.25% ethylene and 34.42% propylene) with the formation of small amounts of BTX aromatics and isobutene over the cracking catalyst loaded in the third-stage reactor.

Items Listing

Embodiments of the present disclosure include at least the following items, which are not intended to limit the scope of the disclosure as a whole or the appended claims.

Item 1: A process for producing olefins from $C_4$-$C_6$ saturated hydrocarbons, the process comprising: passing a feed comprising $C_4$-$C_6$ saturated hydrocarbons and hydrogen into a dehydrogenation unit to produce a dehydrogenation effluent, the dehydrogenation unit comprising a dehydrogenation catalyst; passing at least a portion of the dehydrogenation effluent into a hydrogenation unit to produce a hydrogenation effluent, the hydrogenation unit comprising a hydrogenation catalyst; and passing at least a portion of the hydrogenation effluent into a cracking unit to produce a cracking effluent comprising olefins, the cracking unit comprising a cracking catalyst.

Item 2: The process of Item 1, wherein the feed is preheated to a temperature of from 100° C. to 200° C.

Item 3: The process of Item 1 or Item 2, wherein the dehydrogenation unit operates at a temperature of from 500° C. to 575° C.

Item 4: The process of any of Items 1 to 3, wherein the hydrogenation unit operates at a temperature of from 100° C. to 180° C.

Item 5: The process of any of Items 1 to 4, wherein the cracking unit operates at a temperature of from 400° C. to 550° C.

Item 6: The process of any of Items 1 to 5, wherein the dehydrogenation catalyst comprises platinum on L zeolite.

Item 7: The process of any of Items 1 to 6, wherein the dehydrogenation catalyst comprises tin on L zeolite.

Item 8: The process of any of Items 1 to 7, wherein the hydrogenation catalyst comprises from 0.25% to 7% by weight of a transition metal supported on a support comprising one or more of silica and alumina.

Item 9: The process of any of Items 1 to 8, wherein the hydrogenation catalyst comprises cobalt supported on an alpha-alumina support.

Item 10: The process of any of Items 1 to 9, wherein the cracking catalyst comprises a ZSM-5 catalyst.

Item 11: The process of any of Items 1 to 10, further comprising passing the cracking effluent comprising olefins to a separation unit.

Item 12: The process of any of Items 1 to 11, wherein: the dehydrogenation catalyst comprises platinum or tin on L zeolite; the hydrogenation catalyst comprises from 0.25% to 7% by weight cobalt supported on an alpha-alumina support; cracking catalyst comprises a ZSM-5 catalyst; the dehydrogenation unit operates at a temperature of from 500° C. to 575° C.; the hydrogenation unit operates at a temperature of from 100° C. to 180° C.; and the cracking unit operates at a temperature of from 400° C. to 550° C.

Item 13: A system configured to perform the process of any of Items 1 to 12.

Item 14: A system for producing olefins from $C_4$-$C_6$ saturated hydrocarbons, the system comprising: a dehydrogenation unit in communication with a feed comprising $C_4$-$C_6$ saturated hydrocarbons and hydrogen, the dehydrogenation unit comprising a dehydrogenation catalyst, the dehydrogenation catalyst comprising L zeolite treated with platinum, tin, or both; a hydrogenation unit in communication with a dehydrogenation effluent from the dehydrogenation unit, the hydrogenation unit comprising a hydrogenation catalyst, the hydrogenation catalyst comprising from 0.25% to 7% by weight of a transition metal supported on a support comprising one or more of silica and alumina; and a cracking unit in communication with a hydrogenation effluent from the hydrogenation unit, the cracking unit comprising a cracking catalyst, the cracking catalyst comprising a ZSM-5 catalyst.

Item 15: The system of Item 13 or 14, wherein the hydrogenation catalyst comprises cobalt supported on an alpha-alumina support.

Item 16: The system of any of Items 13 to 15, wherein the dehydrogenation catalyst further comprises a porous support.

Item 17: The system of any of Items 13 to 16, further comprising a separation unit.

It is noted that the terms "substantially" and "about" may be utilized to represent the inherent degree of uncertainty that may be attributed to any quantitative comparison, value, measurement, or other representation. These terms are also utilized to represent the degree by which a quantitative representation may vary from a stated reference without resulting in a change in the basic function of the subject matter at issue.

Unless otherwise defined, all technical and scientific terms used have the same meaning as commonly understood by one of ordinary skill in the art. The terminology used in the description is for describing particular embodiments only and is not intended to be limiting. As used in the specification and appended claims, the singular forms "a," "an," and "the" are intended to include the plural forms as well, unless the context clearly indicates otherwise.

While particular embodiments have been illustrated and described, it should be understood that various other changes and modifications may be made without departing from the spirit and scope of the claimed subject matter. Moreover, although various aspects of the claimed subject matter have been described, such aspects need not be utilized in combination. It is therefore intended that the appended claims cover all such changes and modifications that are within the scope of the claimed subject matter.

What is claimed is:

1. A process for producing olefins from $C_4$-$C_6$ saturated hydrocarbons, the process comprising:
   passing a feed comprising $C_4$-$C_6$ saturated hydrocarbons and hydrogen into a dehydrogenation unit to produce a dehydrogenation effluent comprising corresponding olefins and dienes of the $C_4$-$C_6$ saturated hydrocarbons, the dehydrogenation unit comprising a dehydrogenation catalyst that inhibits isomerization and cracking during the dehydrogenation, the dehydrogenation catalyst comprising platinum and tin on potassium-treated L zeolite;
   passing at least a portion of the dehydrogenation effluent into a hydrogenation unit to produce a hydrogenation effluent, the hydrogenation unit comprising a hydrogenation catalyst that selectively converts the dienes of the $C_4$-$C_6$ saturated hydrocarbons into olefins, the hydrogenation catalyst comprising from 0.25% to 0.5% by weight cobalt on a support comprising silica or alumina, and wherein the hydrogenation unit operates at a temperature of from 100° C. to 180° C. and at atmospheric pressure; and
   passing at least a portion of the hydrogenation effluent into a cracking unit to produce a cracking effluent comprising olefins, the cracking unit comprising a cracking catalyst, the cracking catalyst comprising a ZSM-5 catalyst.

2. The process of claim 1, wherein the feed is preheated to a temperature of from 100° C. to 200° C.

3. The process of claim 1, wherein the dehydrogenation unit operates at a temperature of from 500° C. to 575° C.

4. The process of claim 1, wherein the cracking unit operates at a temperature of from 400° C. to 550° C.

5. The process of claim 1, further comprising passing the cracking effluent comprising olefins to a separation unit.

6. The process of claim 1, wherein:
   the dehydrogenation unit operates at a temperature of from 500° C. to 575° C.; and
   the cracking unit operates at a temperature of from 400° C. to 550° C.

7. The process of claim 1, further comprising:
   passing at least a portion of the cracking effluent to a separator to produce a product stream and a hydrogen stream, the product stream comprising the olefins from the cracking effluent; and
   recycling the hydrogen stream to the feed.

8. A system for producing olefins from $C_4$-$C_6$ saturated hydrocarbons, the system comprising:
   a dehydrogenation unit in communication with a feed comprising $C_4$-$C_6$ saturated hydrocarbons and hydrogen, the dehydrogenation unit comprising a dehydrogenation catalyst, the dehydrogenation catalyst comprising K-L zeolite treated with platinum and tin;
   a hydrogenation unit in communication with a dehydrogenation effluent from the dehydrogenation unit, the hydrogenation unit comprising a hydrogenation catalyst, the hydrogenation catalyst comprising from 0.25% to 0.5% by weight cobalt supported on a support comprising one or more of silica and alumina, and wherein the hydrogenation unit operates at a temperature of from 100° C. to 180° C. and at atmospheric pressure; and
   a cracking unit in communication with a hydrogenation effluent from the hydrogenation unit, the cracking unit comprising a cracking catalyst, the cracking catalyst comprising a ZSM-5 catalyst.

9. The system of claim 8, wherein the hydrogenation catalyst comprises cobalt supported on an alpha-alumina support.

10. The system of claim 8, wherein the dehydrogenation catalyst further comprises a porous support.

11. The system of claim 8, further comprising a separation unit.

* * * * *